United States Patent [19]

Snyder et al.

[11] 4,170,861
[45] Oct. 16, 1979

[54] METHOD AND APPARATUS FOR FILLING PETRI DISHES

[75] Inventors: Philip Snyder, Lawrenceville; David Freedman, Highland Park, both of N.J.

[73] Assignee: New Brunswick Scientific Co., Inc., Edison, N.J.

[21] Appl. No.: 894,317

[22] Filed: Apr. 7, 1978

[51] Int. Cl.² ..................... B65B 3/26; B65B 43/40
[52] U.S. Cl. ................................. 53/468; 53/485; 53/109; 53/282; 53/381 A
[58] Field of Search .............. 53/468, 471, 485, 109, 53/282, 381 A

[56] References Cited

U.S. PATENT DOCUMENTS

| 3,513,621 | 5/1970 | Chamberlin | 53/468 |
| 3,704,568 | 12/1972 | Duhring et al. | 53/109 |

Primary Examiner—Travis S. McGehee
Attorney, Agent, or Firm—Blum, Moscovitz, Friedman & Kaplan

[57] ABSTRACT

A method and apparatus for filling petri dishes include the features of situating a stack of empty petri dishes at a dish-drop station where the stack rests with the lowermost petri dish of the stack on a stationary support. A moving structure engages this lowermost petri dish and moves it beyond the stationary support to a filling station, and during this movement of this lowermost petri dish to the filling station a lower dish member of the petri dish drops down from an upper lid member thereof and remains spaced beneath the upper lid member while being supported by a movable support which carries the lower dish member to the filling station. At the filling station a nozzle of a pump becomes situated in the space between the upper lid member and the lower dish member of the petri dish and fills a given quantity of agar into the lower dish member, whereupon this latter member and the upper lid member spaced thereover are moved to an elevating station. At the elevating station a suitable elevating structure engages the filled lower dish member and raises it into the upper lid member so as to close the filled petri dish, the latter then continuing its upward movement to become situated on a plate. These operations are repeated for each empty petri dish which drops onto the stationary support so that while the empty petri dishes of an empty stack are being removed therefrom one by one to be filled, a stack of filled petri dishes is simultaneously being formed at the elevating station.

24 Claims, 10 Drawing Figures

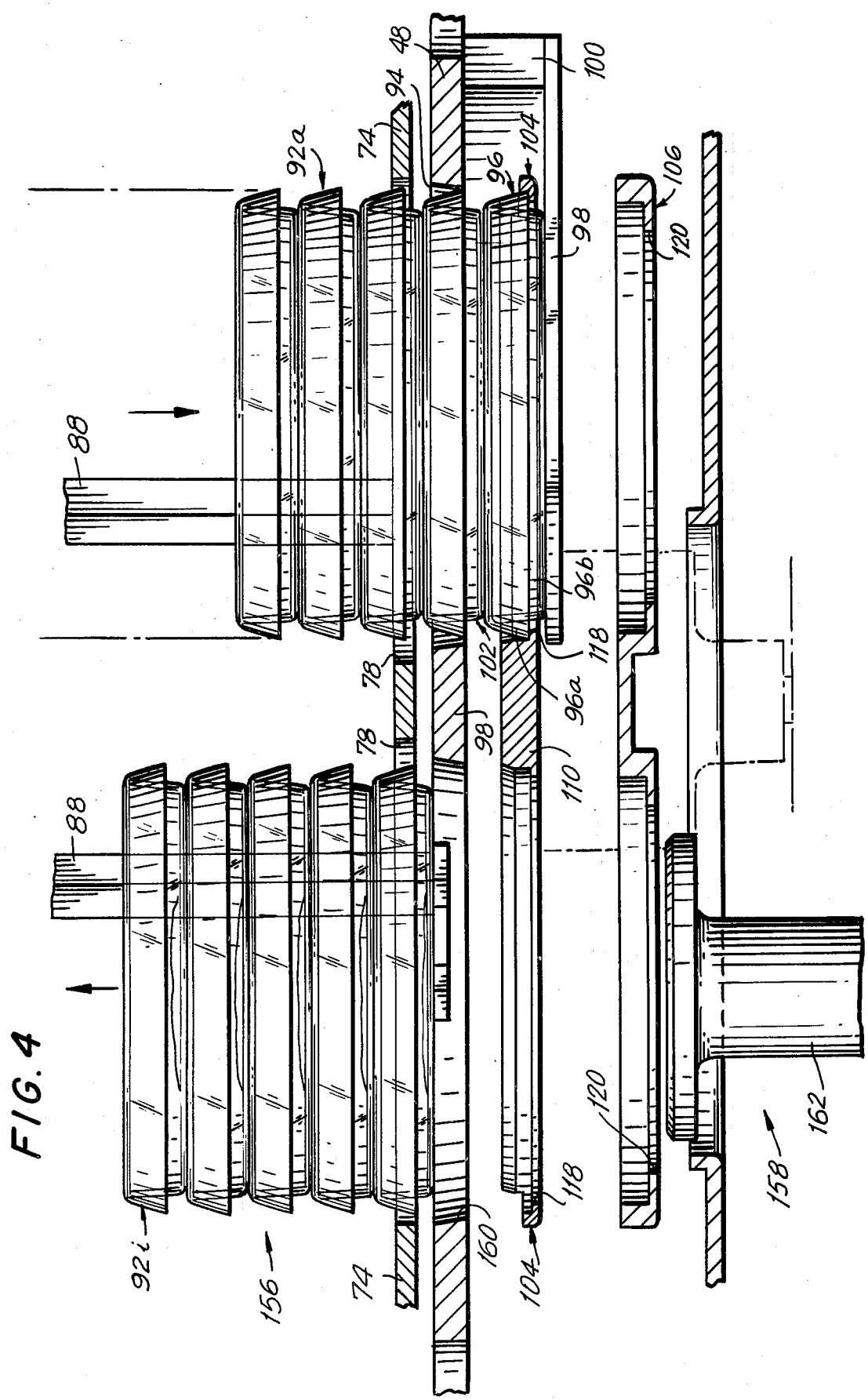

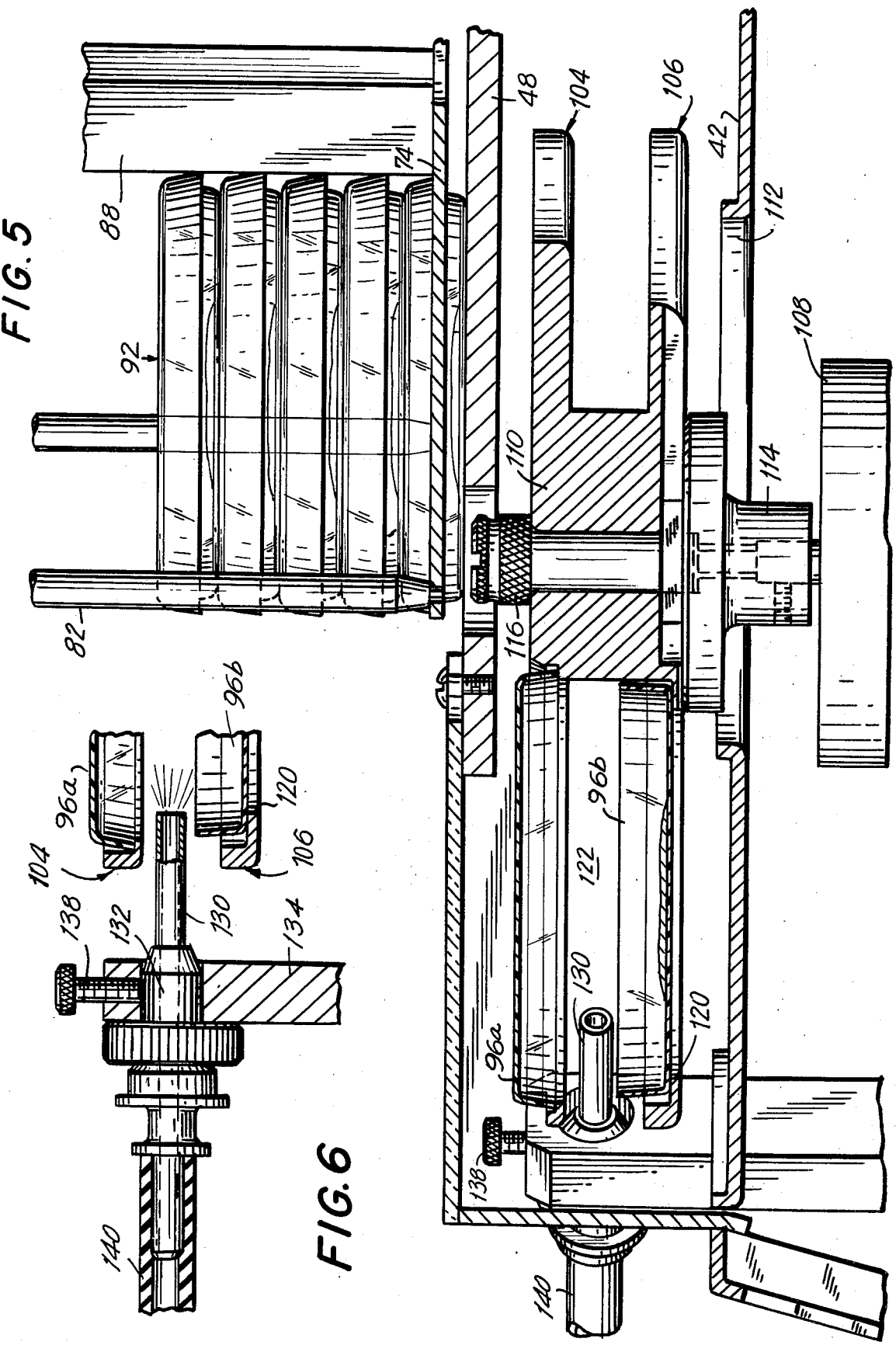

METHOD AND APPARATUS FOR FILLING PETRI DISHES

BACKGROUND OF THE INVENTION

The present invention relates to a method and apparatus for filling petri dishes.

As is well known, in order to detect the presence or absence of certain microorganisms, it is conventional to situate a specimen which may contain the suspected microorganism on a suitable nutrient, usually agar situated in a petri dish. Then the petri dish with the specimen on the agar therein is placed in a suitable incubator where under carefully maintained atmospheric conditions the culture is grown and thereafter examined to determine whether or not certain microorganisms are present.

Petri dishes of the above type are widely used in research and industry. Such petri dishes normally include a lower dish member containing a given quantity of agar and an upper lid member which normally covers the lower dish member. The upper lid member and lower dish member of the petri dishes can be inexpensively manufactured in large quantities inasmuch as they are simply clear plastic components which require only that the upper lid member fit loosely over the lower dish member. However, the costs of petri dishes of the above type are rendered undesirably high because of the procedures required in connection with filling the lower dish member with a given quantity of agar. These procedures require the upper lid member to be removed from the lower dish member, a given quantity of agar to be filled into the lower dish member, whereupon the petri dish is closed by situating the lid member over the filled lower dish member, and of course the agar sets to assume a solid condition upon cooling.

At the present time, the conventional methods and apparatus used in connection with filling petri dishes are relatively complex and time consuming. It is thus difficult to prepare filled petri dishes at a low cost. Furthermore, since the agar is in a liquid condition when it is filled into the lower dish member of the petri dish, care must be taken on one hand to avoid the spilling of the liquid agar and on the other hand to assure that the agar has a uniform depth in the lower dish member of a petri dish. If in an attempt to reduce costs the procedures in connection with filling the petri dishes are carried out too rapidly, spilling of the agar occurs and, particularly where a small amount of agar is situated in a petri dish, the agar does not have a uniform depth.

SUMMARY OF THE INVENTION

It is accordingly an object of the present invention to provide a method and apparatus capable of achieving a rapid, low cost filling of petri dishes.

Moreover, it is an object of the present invention to provide a method and apparatus capable of filling petri dishes in such a way that the agar will not spill and is situated at a uniform depth in each petri dish.

It is a particular object of the present invention to provide an apparatus which is inexpensive and simple as well as extremely compact, while at the same time capable of filling, either according to a batch system or according to a continuous system, a relatively large number of petri dishes with agar or the like in an extremely short time.

In particular, it is an object of the present invention to provide a method and apparatus according to which it becomes possible to load an apparatus with a relatively large number of relatively tall stacks of empty petri dishes, and then turn the apparatus on while it operates automatically in such a way that stack after stack of petri dishes become filled with agar in a rapid reliable manner.

According to the invention, a stack of empty petri dishes is situated on a stationary support which extends beneath the lowermost empty petri dish of the stack. This lowermost dish is then moved away from the stack so that the next higher petri dish drops onto the stationary support with the entire stack dropping down by a distance occupied by a single petri dish. The removed petri dish is transported to a filling station with the upper lid member thereof being spaced from and situated above the lower dish member. At the filling station a filling nozzle extends into the space between the separated upper lid member and lower dish member to fill the lower dish member with a given quantity of agar. Then the lower dish member with the upper lid member still situated above and spaced therefrom are transported to an elevating station where the lower dish member is elevated up into the upper lid member so as to close the filled petri dish, and this closed petri dish is elevated still further to be situated on a plate. The several empty petri dishes of an empty stack are successively treated in this way so that while petri dishes are successively taken from the empty stack, a stack of filled petri dishes is simultaneously being formed.

With the method and apparatus of the invention as soon as one stack of empty petri dishes has become exhausted another stack of empty petri dishes is advanced to take the place of the previous stack of empty petri dishes, and at the same time a filled stack of petri dishes is moved away from the location where the filled stack was formed to provide a space for the next stack of filled petri dishes. By arranging a number of stacks of empty petri dishes at a suitable carousel it is possible to turn the carousel as soon as one stack becomes exhausted so as to situate the next stack in position to be filled, and at the same time the locations previously occupied by the empty stacks of petri dishes become occupied by filled stacks of petri dishes, so that in this way it becomes possible in an extremely small space to provide for rapid filling of a relatively large number of stacks of petri dishes.

BRIEF DESCRIPTION OF DRAWINGS

The invention is illustrated by way of example in the accompanying drawings which form part of this application and in which:

FIG. 4 is a fragmentary section elevation of part of the structure of FIG. 2 taken along line 4—4 of FIG. 2 in the direction of the arrows;

FIG. 5 is a fragmentary section elevation of another part of the structure of FIG. 2 taken along line 5—5 of FIG. 2 in the direction of the arrows;

FIG. 6 is a fragmentary sectional elevation of that part of the structure of FIG. 2 which is situated at the filling station, FIG. 6 being taken along line 6—6 of FIG. 2 in the direction of the arrows;

DESCRIPTION OF THE PREFERRED EMBODIMENTS

Figure 1:
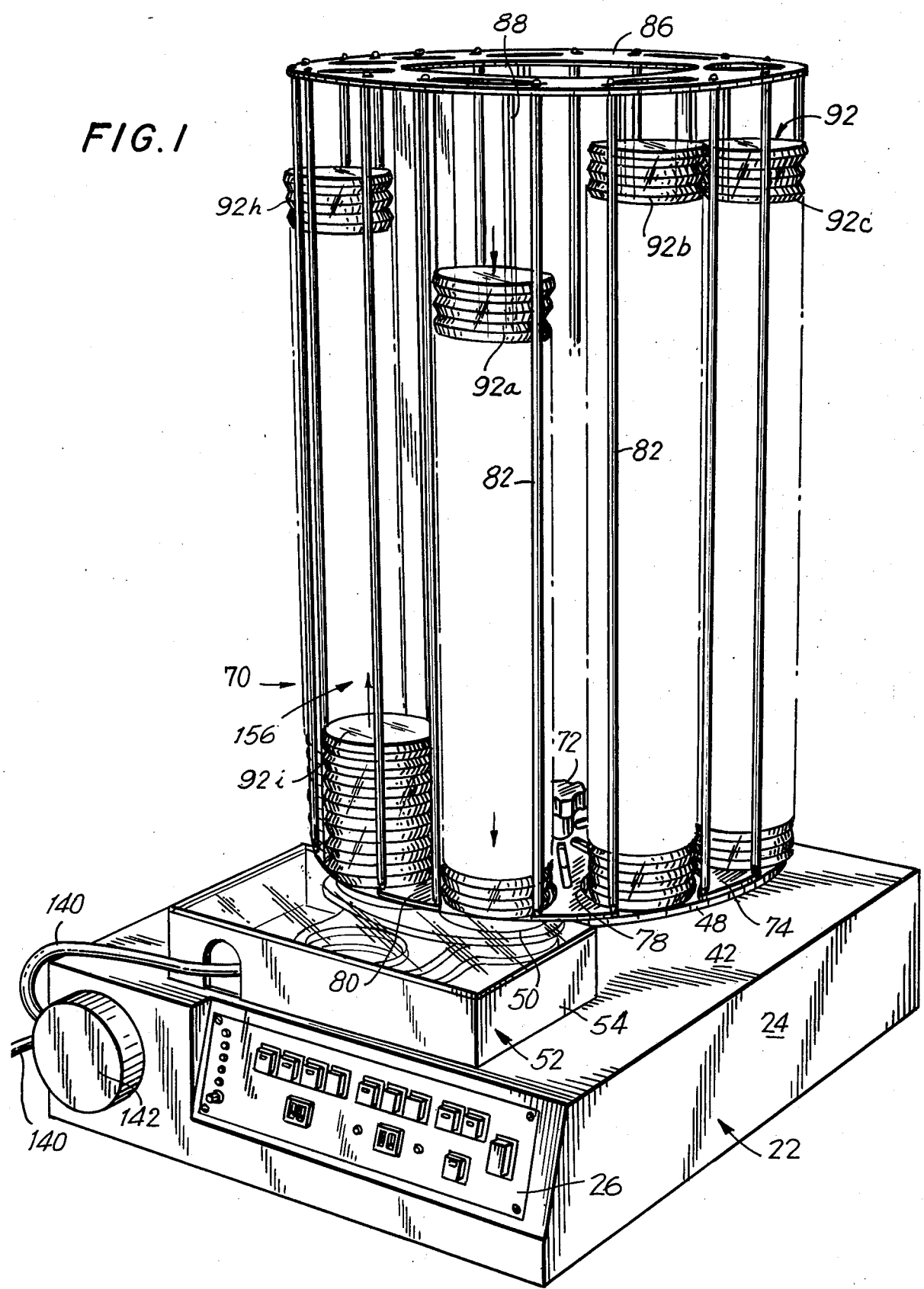
FIG. 1 is a perspective partly schematic illustration of an apparatus of the invention for carrying out the method of the invention.
Figure 3:
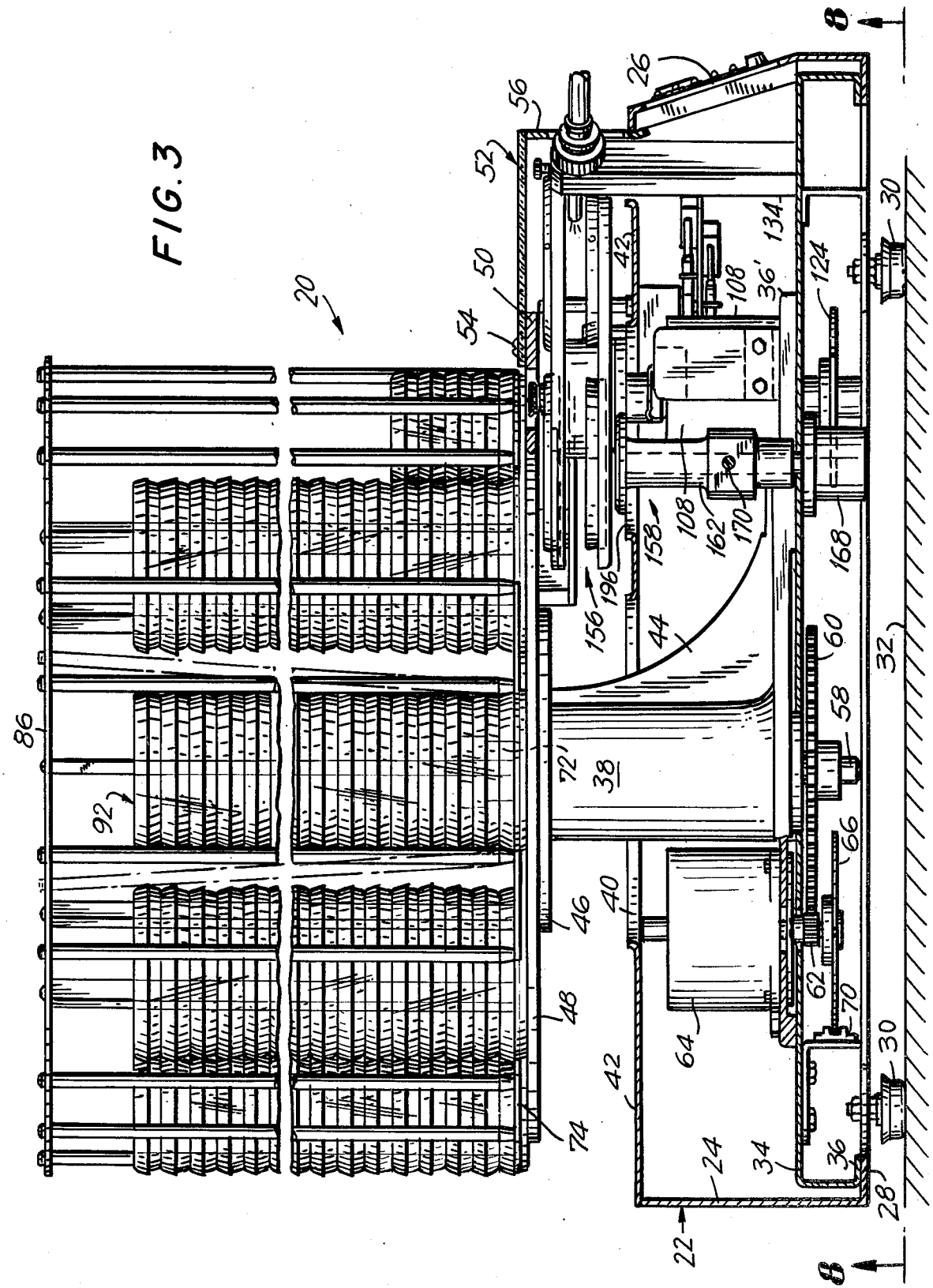
FIG. 3 is a sectional elevation of the structure of FIG. 2 taken along line 3—3 of FIG. 2 in the direction of the arrows.

Referring first to FIGS. 1 and 3, the apparatus 20 of the invention for carrying out the method of the invention includes a lower hollow housing 22 which has an endless side wall 24 of substantially rectangular configuration in plan. The front of the endless side wall 24 of the housing 22 carries a suitable control panel 26. The bottom edge of the side wall 24 is provided with an inwardly extending flange 28 (FIG. 3), and portions of this flange have inwardly extending projections carrying feet 30 (FIG. 3) which rest on any suitable horizontal support 32. Thus, the support 32 may take the form of a suitable table top of which the apparatus of the invention is situated as shown in FIG. 3. The feet 30 are connected to the flange 28 by way of bolts and nuts which may be adjusted for the purpose of levelling the apparatus.

In the hollow housing 22 is an interior supporting structure 34 in the form of a horizontal plate having a downwardly extending side wall terminating also in an inwardly directed flange 36, the latter flange resting on the being fixed to flange 28 so as to be supported by the housing 22 in the interior thereof.

The horizontal support wall 34 in the interior of the housing 22 carries a base plate 36' which is fixed to the support 34 and which is integral with an upwardly extending hollow tubular post 38 which extends upwardly through an opening 40 formed in a top wall 42 of the housing 22. This hollow tubular post 38 may be strengthened by one or more fins 44. The top end of the tubular post 38, which is situated above the wall 42 of the housing 22, is integral with an outwardly directed flange 46, this circular flange 46 fixedly carrying a plate means 48 which is formed with a central opening aligned with the opening of the tubular supporting post 38. Plate means 48 is stationary and of a generally circular configuration except that it has at its front portion a forwardly extending arcuate extension 50 the configuration of which is mostly apparent from FIG. 2.

This dust cover 52 has a pair of opposed side walls 54 which rest on the top surface 42 of the housing 22 while a front wall 56 of the dust cover 52 extends downwardly behind the upper edge of the panel 26, as shown most clearly in FIG. 3.

The tubular supporting post 38 has a lower open end situated in a suitable opening of the supporting wall 34 and supports in its interior, by way of suitable bearings, a rotary drive shaft 58 the bottom end of which is shown in FIG. 3. This rotary drive shaft 58 is supported coaxially within the tubular post 38 by bearings therein in such a way that while the shaft 58 can turn it cannot move axially in a vertical direction.

The shaft 58 carries a gear 60 which is driven by a pinion 62, the pinion 62 being carried by a shaft which extends through an opening of the supporting wall 34 as well as an opening in the base plate 36 which at its top surface to the left of the post 38, as viewed in FIG. 3, carries a driving motor 64 which serves to drive the pinion 62. The shaft which carries the pinion 62 also carries a disc 66 which turns with the pinion 62 and which is formed at its periphery with a single notch 68 (FIG. 8) which travel past an optical sensor 70 of a known construction, this optical sensor cooperating with the notch 68 for timing or calibrating the operation of the motor 64 which is a stepping motor in the sense that it serves to drive the shaft 58 through a predetermined angle each time a signal is delivered to the motor 64 in a manner described below.

The top end of the shaft 58 is situated at an elevation slightly higher than the top surface of the plate means 48, and at its upper portion this shaft 58 is formed with an axial threaded bore which receives the bottom threaded shank of a screw which extends downwardly from the manually turnable knob 72. Thus the bottom threaded shank of the knob 72 may be threaded into the top end of the shaft 58. Clamped between the bottom surface of the knob 72 and the top end of the shaft 58 is the central portion of a lower carousel plate 74 forming part of a carousel means of the invention. Thus the plate 74 is formed with a central opening through which the threaded shank extending from the bottom end of the knob 72 passes, and this knob 72 may be tightened to fix the carousel plate 74 to the shaft 58 for rotary movement therewith. There is provided a suitable locating pin 59 on plate 74 which engages complementary slot 61 for properly indexing the carousel. In the instant embodiment the plate 74 is formed with a series of radially extending slots 76.

The carousel plate 74 is formed adjacent to its outer periphery with a series of openings 78 each of which has the configuration of an almost complete circle. The centers of the circular openings 78 are situated close enough to the periphery of the disc 74 to cause the latter to have at its outer periphery portions of substantially hourglass configuration separating one opening 78 from the next. Thus the openings 78 are themselves open at the outer periphery of the disc 74. Thus the carousel disc 74 has at its outer periphery a series of tongues 80 of substantially hourglass configuration separating the several openings 78 from each other, and these openings are equidistantly situated from each other about the central axis of the lower carousel disc 74. Of course this central axis coincides with the axis of the shaft 58 which turns the carousel means of the invention.

The opposed ends at the outer edge of each tongue 80 are tiltably connected with the bottom ends of upright rods 82 made, for example, of a suitable metal. The bottom ends of the rods 82 are formed with relatively small integral pins passing through relatively small openings in the projections or tongues 80, and these small pins at the bottom end of the rods 82 have in these openings a sufficient clearance to permit tilting of the rods 82 for a purpose referred to below. The top ends of the several rods 82 are received in relatively short arcuate slots 84 (FIG. 2) which pass through and are situated adjacent to the outer periphery of a circular ring or plate 86, these slots 84 all extending along a common circle whose center is in the axis of the shaft 58. The bottom carousel plate 74 fixedly carries at the innermost region of each opening 78 an upright substantially rectangular rigid bar 88, and these bars 88 which are thus fixed at their bottom ends to the lower carousel plate 74 are fixed at their upper ends to the upper ring or plate 86 adjacent to the inner periphery thereof. Thus the ring 86 is fixedly connected with the plate 74, while being parallel thereto, by way of the rigid upright bars 88 which are fixed both to the ring 86 and the plate 74, while the rods 82 are tiltable so as to be movable at their top ends in the slots 84. Leaf springs 90 (FIG. 2) cooperate with portions of the rods 82 extending above the ring 86 so as to urge the top ends of each pair of rods 82 which are situated at the opposite ends of the outer edge of a tongue 80 apart from each other in a manner apparent from FIG. 2.

With the above-described carousel means of the invention it is possible to spread a pair of rods 82 situated at opposite outer ends of an opening 78 apart each other so as to give access to a space defined between each pair of rods 82 and a rigid bar 88 situated behind and between each pair of rods 82. Within this space it is possible to situate a stack of petri dishes 92. Thus by spreading apart a pair of rods 82 adjacent their top ends it is possible to have access to a space which receives a stack of petri dishes 92, with the lowermost petri dish of the stack 92 resting directly on the plate means 48 at an elevation somewhat below the lower carousel plate 74. When the top ends of the rods 82 are in the relaxed position, the springs 90 will expand to displace the top ends of such a pair of rods 82 toward each other in order to confine in this way a stack of petri dishes 92 between a pair of rods 82 and a bar 88. In this way it is possible to situate several stacks of petri dishes 92 in the carousel means of the invention with the several stacks of petri dishes resting on the plate 48 to slide along the top surface thereof when the carousel means is turned by rotation of the shaft 58.

In the illustrated example there are nine pairs of rods 82 with nine bars 88 situated respectively behind the several pairs of rods 82, and of course there are nine openings 78 all equidistantly spaced from each other angularly about the central axis of the carousel means. Thus the carousel means of the invention provides the illustrated example nine stacking positions. In accordance with the invention eight of these stacking positions are initially filled with up to eight stacks of petri dishes 92, and in the particular example of the invention each stack contains up to 40 petri dishes 92, so that before the apparatus is started it can be loaded with up to 320 empty petri dishes occupying eight stacking locations, while one stacking location remains empty for a purpose referred to below. Thus, it will be seen that FIG. 1 shows stacks 92a, 92b, 92c, etc. of empty petri dishes situated one next to the other in a circular row and extending up to the eighth stack 92h of petri dishes, the last stack 92h being spaced from the first stack 92a by a single initially empty stacking station which is shown in FIG. 1 partially occupied by a stack 92i of filled petri dishes. It will be noted that stack 92a is lower than the other stacks by approximately the vertical distance occupied by the stack 92i of filled petri dishes.

In a manner described below the stack 92a of petri dishes is lowered one by one to be successively filled with agar, and the filled petri dishes are elevated into the initially empty stacking location to form the stack 92i of filled petri dishes. When the stacking location occupied by the stack 92a becomes exhausted of empty petri dishes, the carousel means is turned through an angular increment which is sufficient to situate the stack of petri dishes 92b at the location formely occupied by stack 92a, and simultaneously the stack 92i of filled petri dishes is displaced away from the initial location of the empty stacking portion of the carousel means, so that the location previously occupied by stack 92a becomes the empty stacking location to receive the next stack of filled petri dishes which will be supplied from the stack 92b. Of course the empty stacking location is situated at the same angular distance from the first and last stack of petri dishes as the angular distances between the remaining stacks of petri dishes.

Referring to FIG. 4, it will be seen that part of the first stack 92a of empty petri dishes is illustrated therein as well as part of the stack 92i of filled petri dishes. The stack 92a is situated at a dish-drop station of the apparatus of the invention. At this dish-drop station a portion of the plate means 48 is formed with an opening 94 which tapers slightly in a downward direction, and this portion of plate means 48 which is formed with the opening 94 forms a holding means for a purpose referred to below. At this dish-drop station shown at the right of FIG. 4, the stack of empty petri dishes 92a can drop until the lowermost petri dish 96 drops onto a stationary support 98 in the form of a fixed rigid horizontal plate forming a stationary support means for supporting the stack 92a at the dish-drop station. The stationary support means 98 is mounted in cantilever fashion by being fixed at its outer end to a block 100 which in turn is fixed to the lower surface of the plate means 48. Thus the stationary support plate 98 is parallel to the plate means 48 while being situated beneath the latter by a given distance. This distance is such that when the lowermost petri dish 96 of a given stack is on the stationary support 98, the next higher petri dish 102 is situated in the opening 94. In a manner described below this lowermost dish 96 is displaced horizontally beyond the stationary support means 98 while the portion of the plate means 48 formed with the opening 94 acts as a holding means to hold the next higher dish 102 against horizontal movement with the lowermost dish 96, so that in this way it is only the dish 96 which is displaced from the bottom end of the stack of empty petri dishes at the dish-drop station. After this lowermost petri dish moves horizontally beyond the next higher dish 102, this next higher dish 102 is free to drop onto the stationary support means 98.

The lowermost petri dish 96 of the empty stack 92a at the dish-drop station is moved horizontally beyond the stationary support 98 by way of a moving means 104 which extends in part between the portion of the plate means 48 which forms the holding means for the dish 102 and the stationary support 98. This moving means 104 is formed by an upper plate member of a rotary turntable 110 which includes a lower plate member 106 forming a movable support means described in greater detail below. As is shown in FIG. 5, the upper plate member 104 and the lower plate member 106 are fixed to each other for movement together about a common upright axis, a suitable stepping motor 108 being operatively connected with the turntable 110 which includes the upper plate member or moving means 104 and lower plate member or movable support means 106.

Thus as is shown most clearly in FIG. 5 the upper wall 42 of the housing 22 is formed with an opening 112 through which a support 114 for the turntable 110 extends. This support 114 is fixed to the top end of the output shaft of the motor 108. A screw 116, the head of which is situated in an opening of the plate means 48, extends through a central bore of the turntable 110 and serves to fix the turntable 110 to the support 114 which is turned together with the table 110 by way of the motor 108. The upper plate member or moving means 104 is formed with three openings 118 which are equidistantly spaced from each other by 120° about the central axis of the turntable 110. The size of each opening 118 is such that the upper lid member 96a of the lowermost petri dish 96 cannot move through the opening 118 while at the same time the lower dish member 96b can pass freely through the opening 118 to rest on the support 98. Thus, when the turntable 110 is turned to displace the lowermost petri dish 96 horizontally beyond the stationary support 98, the lower dish member 96b can drop downwardly beyond the upper lid member 96a, and this lower dish member 96b will drop onto the movable support means 106 formed by the lower plate member of the rotary turntable 110.

This lower plate member 106 is itself formed with three equidistantly spaced openings 120 aligned beneath the openings 118 and being of a smaller diameter than the openings 118. The diameter of the openings 120 is such that the lower dish member of each petri dish will rest at its outer periphery on the lower plate member 106 in alignment with the opening 120, the arrangement of the lower dish member 96b on the lower movable support 106 being shown most clearly at the left of FIG. 5 where the lower dish member 96 is shown at a filling station with the upper lid member 96a being spaced over and aligned with the lower dish member 96b in the manner shown in FIG. 5.

Thus with the structure of the invention when the turntable 110 turns it will displace the lowermost petri dish of an empty stack beyond the stationary support 98 toward the filling station 122 shown in FIG. 5, and during this transportation of the lowermost petri dish toward the filling station from the dish-drop station, the lower dish member of the petri dish will drop down from the upper lid member thereof onto the lower movable support 106 which thus serves to transport the dropped dish member 96b with the upper lid member 96a while maintaining these members vertically spaced from each other as illustrated.

Figure 2:
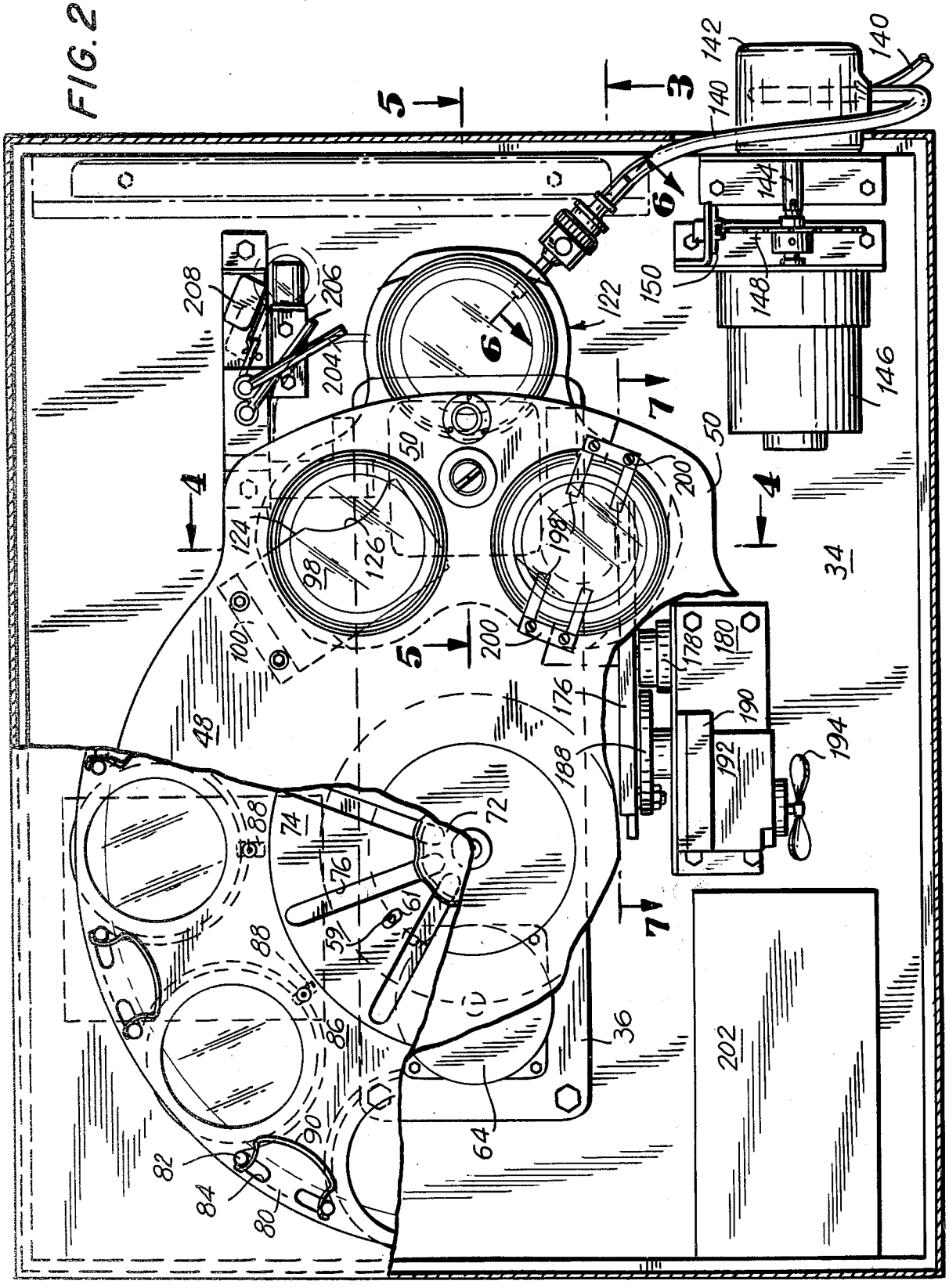
FIG. 2 is partly sectional and partly broken away top plan view of the structure of FIG. 1.

As may be seen from FIG. 2, the edge 124 of the stationary support plate 98 is formed with an arcuate cutout 126 which permits the lower dish member of the lowermost petri dish to drop earlier than if the edge 124 were straight. As soon as the lowermost petri 96 moves beyond the next petri dish 102, the latter drops down onto the top of the turntable 110 and then through the next opening 118 onto support 98. Of course the entire stack 92a moves down by an increment equal to the height of one petri dish.

Figure 8:
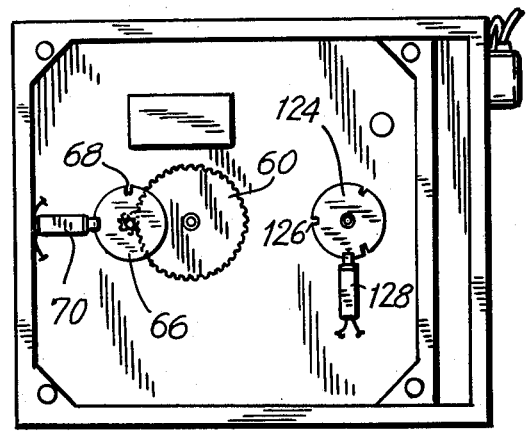
FIG. 8 is a schematic bottom plan view of the structure of FIG. 3 taken along line 8—8 of FIG. 3 in the direction of the arrows.

The stepping motor 108 which turns the turntable 110 is connected to any suitable source of current and is carried by the base plate 36. The shaft of this motor 108 extends downwardly through an opening in the base plate 36 and an opening in the support wall 34 to be situated at its lower end beneath the wall 34. Beneath this wall 34 this shaft of the motor 108 fixedly carries an optical control disc 124 formed at its outer periphery with notches 126 (FIG. 8). The periphery of the disc 124 passes through an optical sensor 128 carried by the wall 34 beneath the latter. This structure also is regulated so that by cooperation of the optical sensor 128 with the notches 126 the turntable 110 will be turned through a given increment.

According to one of the features of the present invention, the optical disc 124 and the optical sensor 128 cooperate with each other for turning the turntable 110 through an angle of 120° after each dwell interval of the turntable 110. However, during this turning at each advance interval of the turntable 110, an abrupt interruption in the turning movement is provided so that the turning movement of the turntable 110 at each advance interval is at least partly abruptly interrupted for an instant. Thus each time the turntable 110 is turned it turns first through approximately 60°, then abruptly stops for an instant, and then continues turning through the remaining 60°. The turntable 110 is turned in this manner during each advancing interval so that agar which has been filled into the lower dish member of a petri dish at the filling station 122 will by the inertia created during the abrupt stop at each advance interval become more uniformly spread in the lower dish member so as to assure in this way that the agar has a uniform depth in the lower dish member of each filled petri dish.

At the filling station 122, a nozzle extends into the space between the upper lid member 96a and the lower dish member 96b of the petri dish at the filling station. Thus the distance between the upper lid member and lower dish member of a petri dish is such that the nozzle 130 can freely be received in the space between these members as indicated in FIGS. 5 and 6.

The nozzle 130 is in the form of a stationary tubular member which extends through and is carried by a fitting 132 (FIG. 6) fitted into an opening at the upper region of a stationary post 134, and held therein by a set screw 138. Fitting 132 engages post 134 and defines a stop to determine the terminal position of nozzle 130. The supporting post 134 is fixed to and extends upwardly from the supporting wall 34 in the manner most clearly apparent from FIG. 3. It will be seen that the upper wall 42 of the housing 22 is also formed with an opening through which the post 134 extends.

The nozzle 130 forms an extension of a flexible hose 140 which extends from and forms the output of a pump 142 which is mounted in an opening of the front wall of the housing 22. A portion of the hose 140 extends outwardly beyond the pump 142 to communicate with a supply of agar. The pump 142 is of the type which has in its interior rollers which are rotated and successively compress the portion of the hose 140 situated within the pump 142, so that this hose 140 is closed at a plurality of successive portions which together move along the hose 140 to create in this way the pumping action in a well known manner. These rollers are driven by a shaft 144 (FIG. 2) which in turn is driven by way of a motor 146. This motor 146 may be mounted on the supporting wall 34. The motor 146 also drives an optical calibrating disc 148 which is a disc of the same construction as the optical discs 60 and 124. The notches at the periphery of the disc 148 turn through an optical sensor 150 carried by a suitable bracket as shown in FIG. 2.

By way of a calibrating button 152 and volume indicator 154 at the control panel 26 (FIG. 9) it is possible in a known way to provide for operation of the pump 142 each time a petri dish is situated at the filling station, during a dwell interval of the turntable 110, with the calibration being such that a preselected volume of agar will be filled into the lower dish member of each petri dish which thus becomes situated at the filling station.

After a petri dish at the filling station has thus become filled with a given quantity of agar, during a dwell interval of the turntable 110, the stepping motor 108 is actuated to again turn the turntable 110 through the next advancing interval, and at this time the next empty petri dish is brought up to the filling station in the manner described above, while the filled petri dish is advanced from the filling station to an elevating station 156. At the elevating station 156 an elevating means 158 operates to elevate the filled lower petri dish member up into the lid member situated thereover, with the elevating means 158 continuing to elevate the thus-closed petri dish upwardly through an opening 160 (FIG. 4) in the stationary plate means 48, so as to become situated in the stack 92i which forms at the previously empty stacking location of the carousel means of the invention.

Figure 7:
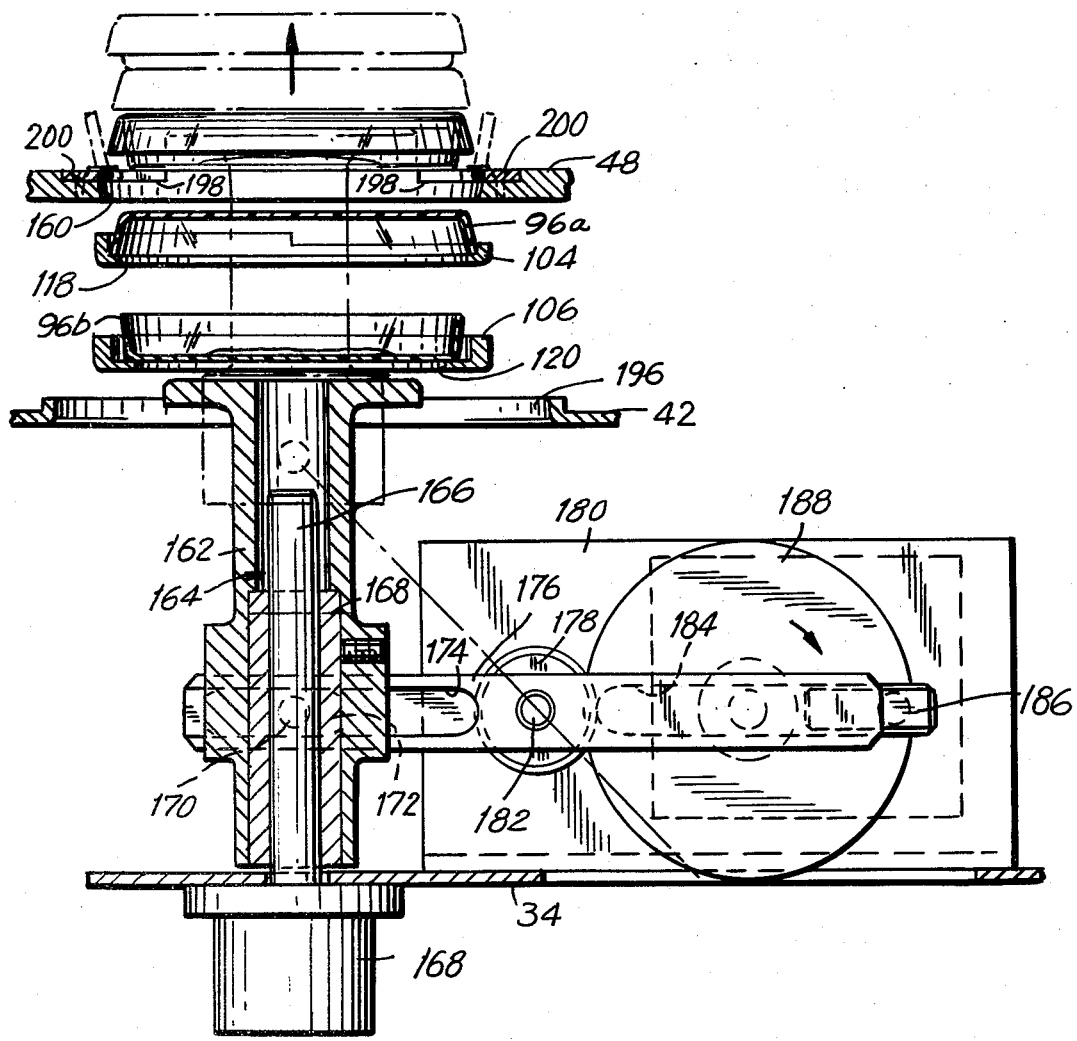
FIG. 7 is a fragmentary sectional elevation of the elevating station of the invention, FIG. 7 being taken along line 7—7 of FIG. 2 in the direction of the arrows.

The elevating means 158 includes an elevating plunger 162 which is guided for vertical movement by a guide means 164 which includes an upright rod 166 fixedly carried by and extending upwardly from a support 168 fixed to the lower surface of the supporting wall 34. The guide rod 166 extends from the support 168 upwardly through an opening in the wall 34 as shown most clearly in FIG. 7. The plunger 162 has an elongated hollow tubular portion which fixedly carries in its interior a guide sleeve 168. The guide rod 166 is suitably keyed so that the plunger 162 cannot turn about the guide rod 166. The plunger 162 carries at one side a pivot pin 170 on which a slide block 172 is freely turnable. This block 172 is capable of sliding in an elongated groove 174 formed in a lever 176 which is pivotally supported intermediate its opposed ends by a pivot pin 182 supported in a bearing 178 carried by a bracket 180 which is mounted on the wall 34. FIG. 7 shows the substantially central pivot 182 of the lever 176.

In the same way, the lever 176 is formed distant from the guide groove 174 with a second guide groove 184, and a second slide block 186 is slidable within the groove 184. This block 186 is pivotally carried by a rotary disc 188, being eccentrically mounted thereon distant from the central turning axis of the disc 188. The disc 188 is supported for rotation about its axis on a wall of the bracket 180 and is driven through a gear transmission 190 from a motor 192 (FIG. 2). This motor 192 also serves to operate a cooling fan 194.

When the motor 192 is set into operation during a dwell interval of the turntable 110, the disc 188 is turned in a clockwise direction, as shown by the arrow in FIG. 7, so that the right end of the lever 176 in FIG. 7 swings downwardly while the left end thereof swings upwardly, to cause the plunger 162 to be raised. The plunger 162 can move freely through an opening 196 formed in the upper wall 42 of the housing 22. At each dwell interval of the turntable 110, an opening 120 of the movable support means 106 becomes aligned above the plunger 162. Thus when the latter moves upwardly, it will raise a filled lower petri dish member 96b (FIG. 7) upwardly into the lid member 96a situated thereover. The diameter of the opening 120 is of course larger than the diameter of the upper enlarged end of the plunger 162. The upward stroke of the plunger 162 is such that not only will it lift the filled lower petri dish member into the upper lid member, but in addition the thus-closed, filled petri dish will be raised upwardly through the opening 160 in the stationary plate means 48 to a given elevation above the plate means 48, whereupon the continued rotation of the disc 188 will result in downward return movement of the plunger 162 to the solid line position shown in FIG. 7 where, while the top end of the plunger 162 is situated slightly above the upper housing wall 42, it is nevertheless slightly below the movable support means 106. Of course the plunger 162 returns to its lower rest position before the next advancing interval of the turntable 110.

The stationary plate means 48 carries at its opening 160, which is situated at the elevating station 156, a means which will prevent downward movement of a raised petri dish beyond the plate 48. For this purpose the plate 48 carries at diametrically opposed portions of the opening 160 a pair of hinged members 198. These members 198 are hingedly supported on plates 200 which are suitably bolted to the top surface of the plate 48. Suitable wire springs urge the members 198 to the lower solid line position thereof shown in FIG. 7 where they are flush with the top surface of the plate 48. The construction of the members 198 and plates 200 is such that the members 198 cannot turn downwardly beyond the horizontal positions thereof shown in solid lines in FIG. 7, while at the same time they can turn in opposition to the springs acting thereon upwardly to the dotted line positions shown in FIG. 7. The maximum elevation to which each petri dish is raised by the plunger 162 is such that at this maximum elevation the springs can act on the members 198 to return them to their lower positions. The maximum diameter of the enlarged top end of the plunger 162 is such that it can move freely past the members 198 when they are in their lower solid line position shown in FIG. 7. As is apparent from FIG. 2, each hinged member 198 has a pair of spaced fingers so that these hinged members 198 will provide a stable support for a stack of filled petri dishes. Thus, each filled and closed petri dish will move downwardly from its maximum elevation part of the way with the downwardly moving plunger 162 until the petri dish rests on the fingers of the hinged members 198, and in this way the last petri dish to be elevated into the previously empty stacking location of the carousel means becomes situated at the bottom of the stack of filled petri dishes 92i which is being formed. Of course the entire stack of filled petri dishes 92i will be raised and lowered each time an additional petri dish is added to the bottom thereof. It will be noted from FIG. 1 that the several stacks of petri dishes extend to a height which is somewhat below the upper plate or ring 86 of the carousel means, so that in this way clearance is provided for the vertical displacement of the stack of filled petri dishes even when the last petri dish has been added to the bottom thereof. Of course in the illustrated example this last petri dish will be formed by the uppermost petri dish of the stack 92a after this latter petri dish has been filled.

All of the above motors, optical sensor controls, and elements at the control panel 26 are connected in an unillustrated manner to a programming unit situated, for example, in a control box 202 on the supporting wall 34 (FIG. 2). Assuming that the carousel means of the invention is empty and the machine turned off, the operator will fill all of the stacking locations with petri dishes, except the stacking location which is situated at the elevating station 156. Of course it is assumed that the hose 140 has been placed in communication with a source of agar which is in a condition to be pumped. Naturally the first stack 92a will drop down so that the lowermost petri dish thereof will become situated on the stationary support 98. Now the machine through the controls provided by way of the program system of the above-described structure of the invention, operating according to the method of the invention, will bring about turning of the turntable 110 through an initial advancing interval to situate a petri dish at the filling station, and then through the controls of the apparatus the lower dish member of this petri dish at the filling station is provided with a given quantity of agar during the first dwell interval of the turntable 110. The plunger 162 at this time may go through a complete operating cycle without raising a petri dish. However, during the next advancing interval, the previously filled petri dish is brought into alignment with the plunger 162, so that this plunger operates at the next dwell interval to situate the first filled petri dish at the elevating station on the stationary plate means 48. These operations go forward continuously with the controls being such that after the turntable 110 has received all the petri dishes from one stack, e.g. stack 92a, a signal is transmitted to the motor 64 to bring about turning of the carousel through the angle required to bring the second stack of petri dishes into the location occupied by the first stack. In this way the operations go forward from one stack to the next without interruption, and the apparatus is automatically stopped as soon as eight complete stacks of petri dishes, in the above example, have been completely filled. Then the apparatus can be permitted to remain stationary so as to assure that the agar becomes solidified in all of the petri dishes. Then the operator will remove all of the stacks of filled petri dishes from the apparatus of the invention and replace the filled stacks with empty stacks after which the apparatus is again turned on to repeat the above operations.

The programming type of control system utilized with the structure of the invention is made up of a number of logic and microprocessor components which operate not only to continuously bring about the above operations in connection with the separate petri dishes in a fully automatic manner but which also can respond to detection of improper operation so as to stop the apparatus and indicate to the operator which is wrong so that the operator will know how to set about to correct the faulty operation and again start the operation of the machine. For example, as part of the fail-safe and control system there are shown in FIG. 2 a pair of swingable fingers 204 and 206. As is apparent from FIGS. 2, 5 and 7, when the lower dish member of a petri dish has been situated below the upper lid member thereof, both of these members extend beyond the turntable components which carry them. Thus it will be seen that the upper dish member 96a extends somewhat beyond the moving means formed by the plate 104 while the lower dish member 96b extends beyond the movable support means 106. The upper finger 204 is situated in the path of movement of the upper lid member 96a to the filling station, while the lower finger 206 is situated in the path of movement of the lower dish member 96b to the filling station, the upper and lower plate members 104 and 106 turning laterally adjacent the fingers 204 and 206, respectively, so that these fingers 204 and 206 can detect the presence of the upper lid member and lower dish member of each petri dish. When such presence is detected, the fingers 204 and 206 are turned on pivotal supports and serve to actuate microswitches, respectively, the microswitch 208 for the finger 204 being indicated in FIG. 2. The program system can detect when a microswitch is not actuated by one of the fingers. Thus a signal will be given, for example, that for some reason the lower dish member has not separated from the upper lid member, or if there is a lower dish member, then there is not an upper lid member thereover, and so on. Thus, the apparatus of the invention is set up with suitable fail-safe devices to detect improper operation.

However, when both fingers 204 and 206 simultaneously fail to detect the presence of an upper lid and lower dish member, a signal is transmitted to motor 64 to turn the carousel, since the fingers detect at this time that a stack is exhausted. At the same time the program system controls the pump so as not to deliver agar when the empty parts of the turntable arrive at the filling station.

It is to be noted in this connection that there are available on the market only a relatively small number of types of petri dishes which differ from each other to such a small extent that the apparatus of the invention can operate properly with most of the petri dishes presently available on the market.

Figure 9:
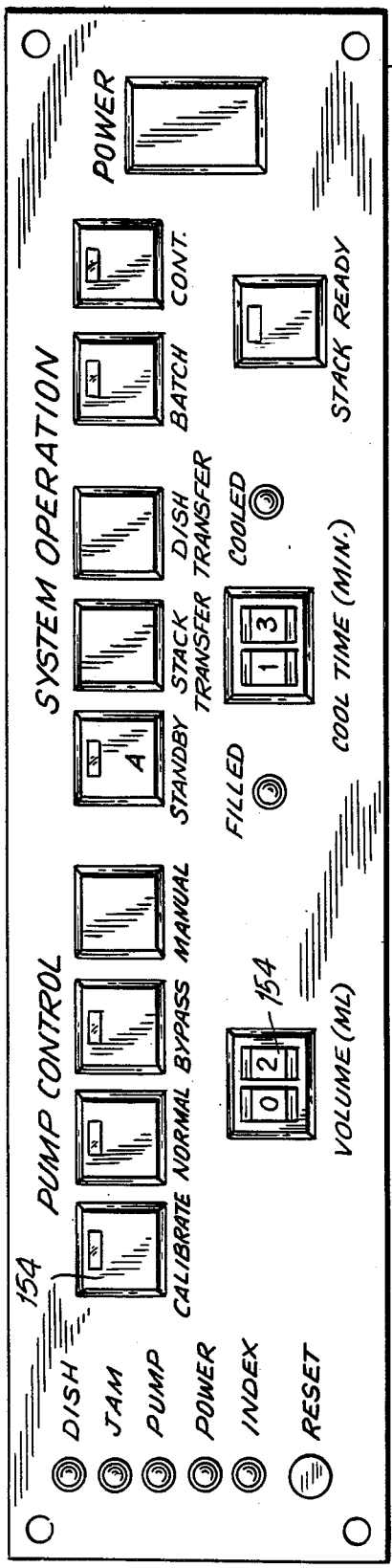
FIG. 9 is an illustration of a control panel forming part of the apparatus of the invention.

As is apparent from FIG. 9, the control panel 26 is provided at its left portion, as viewed in FIG. 9 with a number of lamps which become automatically illuminated when certain troubles are encountered. Thus the sensing fingers 204 and 206 will result in illumination of the upper dish lamp shown in FIG. 9, in the event that a problem is encountered in connection with lack of part of a petri dish as described above. Any jamming will result in illumination of the next lower lamp, while trouble at the pump, trouble with the power supply, or trouble with the indexing system will result in illumination of the corresponding lamps. When the trouble is eliminated the lower reset button shown at the left of FIG. 9 can be actuated to again resume the operation.

The calibration button 152 of the pump controls have been referred to above. These pump controls also include a normal operating button, as well as a bypass button and a manual button. The normal button is of course utilized for normal operation of the pump. The bypass button is utilized when there is an interruption in the operation, and it is desired to continue pumping the agar so that it will not solidify and so that an assurance is given that the pumping operations are going forward properly. For this purpose the nozzle 130 is removed from the fitting 132, and this nozzle may simply be placed in communication with the source from which the agar is drawn by the pump 142 or with a waste receptable. With the parts in this bypass position the agar can be pumped and returned to the source thereof so as to assure proper flow and so as to maintain the agar in its flowing condition if there is an interruption in the operation, thus preventing occurrence of solidification of agar in the hose 140, for example. The pump can also be manually controlled by the manual botton indicated in FIG. 9, when used independently.

FIG. 9 shows at the right various buttons for batch and continuous operation as well as for turning the power on and for indicating when a stack is ready in connection with continuous operation, for example. Also it will be seen that a suitable cooling time can be set with lamp indicators being provided to show that all of the petri dishes have been filled and also to indicate when the cooling time has elapsed so that it is indicated by the lamp at the right of the cooling time that the required cooling time has elapsed. Furthermore, the system operation includes buttons for providing standby, stack transfer, and dish transfer operation.

Figure 10:
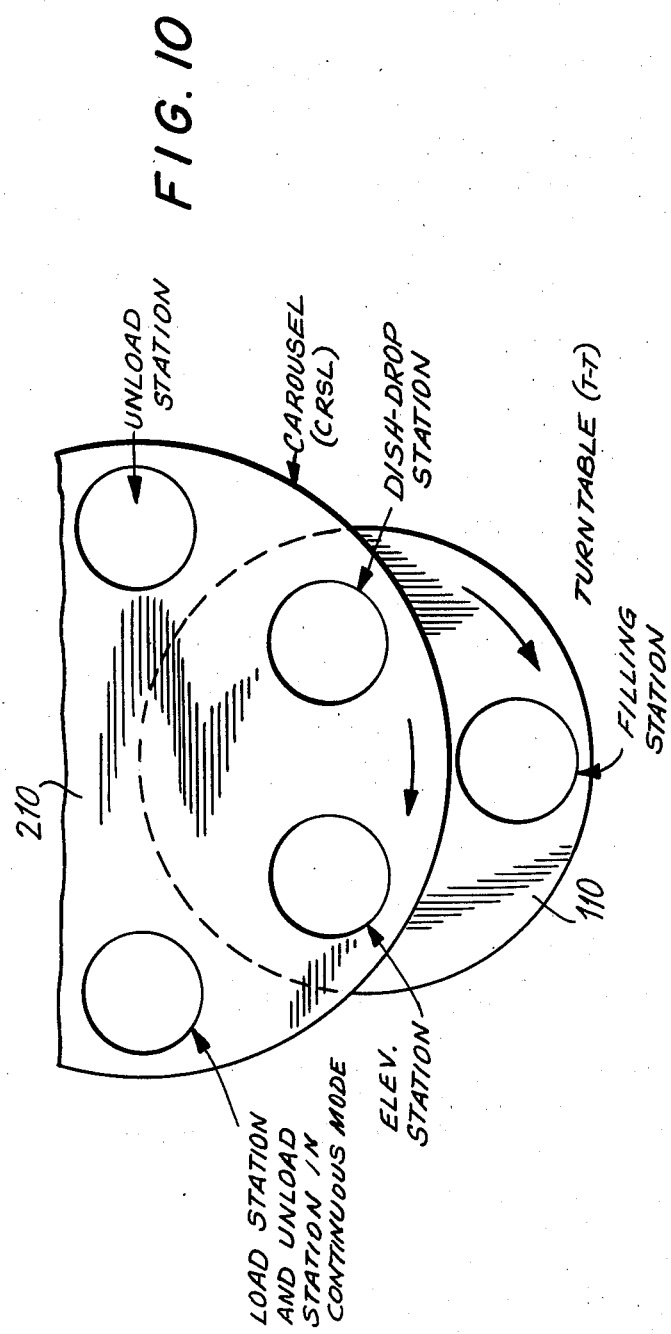
FIG. 10 is a schematic representation of part of the method and apparatus of the invention.

The manner in which the apparatus and method of the invention operates both in a continuous as well as in a batch mode are schematically indicated in FIG. 10 where the carousel means 210 of the invention is schematically illustrated together with the turntable 110. Thus whether the apparatus and method of the invention are utilized in the continuous or batch mode, a petri dish at the dish-drop station is turned outwardly away from beneath the carousel means 210 to a location forwardly thereof where the filling station is located as indicated in FIG. 10, and then the filled petri dish is transferred from the filling station to the elevating station to again become situated beneath the carousel means 210. When operations have been completed in the batch mode, according to which all of the stacks of petri dishes have been filled, the apparatus automatically stops, the stacking location at the dish-drop station remains empty and each stack of filled petri dishes can be unloaded after the cooling time referred to above has elapsed, at the unload station in the batch mode indicated in FIG. 10. Thereafter all of the stacking locations except that at the elevating station are filled with petri dishes, at the load station in batch mode indicated in FIG. 10, and the operations are resumed.

When operating in the continuous mode, petri dishes which are to be filled are initially loaded into the stacking location situated at the position of the stack 92h in FIG. 1, this being designated at the load and unload station in continuous mode in FIG. 10. Then the number of petri dishes which form the stack in the continuous mode is transferred by operation of the stack transfer button to the dish-drop station and at this station the carousel remains stationary while the turntable 110 is turned by the dish transfer button after each petri dish has been filled and situated at the elevating station. While operating in the continuous mode, once each petri dish drops at the dish-drop station, the operations will forward automatically until the particular petri dish has been filled and situated at the elevating station. In the above manner when operating in the continuous mode the filled petri dishes will become located at the elevating station, and then the stack transfer button is operated to locate the filled stack at the unload station in the continuous mode indicated in FIG. 10, this being the station just beyond the elevating station, and at this location the petri dishes which have been filled in the continuous mode can be unloaded and additional empty petri dishes can be loaded.

It is thus apparent that with the method and apparatus of the invention an extremely flexible arrangement has been provided according to which it is possible either to operate in a continuous batch mode and according to which the operations will go forward unless certain faults unexpectedly occur, in which case a fail-safe part of the system of the invention operates to detect the improper operation and stop the operation of the apparatus until the flaw has been corrected. It will be noted that particularly by way of the above-described carousel means 210 and the turntable system cooperating therewith it is possible to bring about continuous filling of a large number of petri dishes with an apparatus which occupies an extremely small space and which is relatively simple. The top surface of the plate means 48 has a low coefficient of friction with respect to the petri dishes so that only a relatively small amount of power is required to turn the carousel means, and in addition relatively small power is required for the remaining operation so that the method and system of the invention utilize only a relatively small amount of power.

Moreover, many variations are possible with the method and apparatus of the invention. Thus any desired number of stacking locations may be provided at the carousel means, and with any number of petri dishes in each stack the program system of the invention operates so that as each stack is exhausted at the dish-drop station the program means will operate to advance the carousel through the increment required to situate the next stack at the dish-drop station. In this connection it is also possible to utilize, instead of detecting fingers, other systems such as an optical type of photocell system situated, for example, to detect when the last petri dish of a given stack has moved beyond the opening 94 of the plate means 48, so that in response to a signal from such a detector it is possible also to bring about operation of the motor 64 to turn the carousel means through the required increment. In addition, it is not essential to provide for the turntable 110 angular increments of turning through 120°, with only three locations being provided for the dishes at the turntable 110. For example it is possible to provide a turntable with four such locations respectively displaced at uniform angles of 90° from each other angularly about the axis of the turntable, with the operations going forward in such a way that at every 90° increment of turning another petri dish becomes located at the filling station as well as at the elevating station. In other words with such a system at each dwell interval there will be a petri dish between the dish-drop station and the filling station ready to move to the filling station at the next advancing interval, while they will also be a filled petri dish between the filling station and the elevating station ready to move to the elevating station at the next advancing interval. Thus, the method and apparatus of the invention are easily adapted to variations of the above type.

What is claimed is:

1. In a method for filling petri dishes each with a given quantity of agar, wherein each petri dish includes a lower dish member and an upper lid member normally covering and extending loosely downwardly around the exterior of the dish member, the steps of situating a stack of empty petri dishes at a dish-drop station while supporting the lowermost petri dish of the stack on a stationary support with all of the remaining petri dishes of the stack at the dish-drop station resting on the lowermost petri dish, displacing the lower-most petri dish horizontally beyond the stationary support while preventing the next petri dish directly above the lowermost petri dish from being displaced with the latter and freeing said next petri dish to drop onto said stationary support as soon as the lowermost petri dish has been moved horizontally beyond said stationary support, so that the entire stack drops onto the stationary support as soon as the lowermost petri dish has been displaced beyond the stationary support, situating beneath the lowermost petri dish which has been displaced from said stationary support a movable support onto which the lower dish member of the lower-most petri dish falls, while simultaneously preventing the lid member of the lowermost petri dish from falling with the lower dish member thereof and maintaining the lid member, from which the lower dish member drops, vertically aligned above the lower dish member, and moving the lower dish member, by way of the movable support, and the lid member aligned with said lower dish member, while they are vertically spaced from each other, to a filling station where a filling nozzle extends into the space between the lower dish member and upper lid member, filling a predetermined quantity of agar into the lower dish member at the filling station from said nozzle, then displacing the filled lower dish member, while maintaining the upper lid member vertically aligned therewith and spaced therefrom, by way of said movable support to an elevating station, elevating the lower dish member which is at the elevating station upwardly into the lid member situated thereover for closing the filled petri dish, and then continuing the elevation of the closed petri dish up to and beyond a predetermined elevation while preventing downward movement of the filled petri dish below said predetermined elevation, and repeating the above steps with each petri dish which drops onto the stationary support so that while a stack of empty petri dishes is being lowered one by one and becomes of a progressively smaller height, at said stationary support, a stack of filled petri dishes is being formed one by one and has a gradually increasing height, at said elevating station.

2. In a method as recited in claim 1 and including the steps of situating a second stack of empty petri dishes at said dish-drop station as soon as the empty petri dishes of a stack previously situated at said dish-drop station becomes exhausted, and displacing a filled stack of petri dishes at the elevating station away from the latter to provide at the elevating station a free space to receive the next stack of filled petri dishes formed from the empty petri dishes taken from the second stack.

3. In a method as recited in claim 2 and including the steps of initially arranging a number of stacks of empty petri dishes at equal angular distances from each other around a predetermined upright axis in a circular row with the first stack of the circular row situated at the dish-drop station while the last stack of the row is situated just beyond the elevating station so that the latter remains free to receive filled petri dishes formed from the empty petri dishes taken from the first stack of the circular row, and after each stack of petri dishes has become exhausted at said dish-drop station and has formed a filled stack of petri dishes at the elevating station, turning all of the stacks simultaneously about said axis for situating the stack next to the first stack at the dish-drop station while displacing the filled stack away from the elevating station, and continuing the above operations until all of the stacks of petri dishes become filled.

4. In a method as recited in claim 1 and including the step of turning the movable support with the lower dish member of a petri dish thereon, while maintaining the lid member thereof above and spaced over the lower dish member, first to said filling station and then to said elevating station.

5. In a method as recited in claim 4 and including the steps of filling a lower dish member at the filling station while elevating a filled dish member at the elevating station.

6. In a method as recited in claim 5 and including the step of displacing a lowermost petri dish at the dish-drop station from said stationary support while simultaneously turning a filled dish member with a lid member spaced thereabove from the filling station to the elevating station and simultaneously transporting the dropped lower dish member and the lid member thereover from the dish-drop station to the filling station so that the operations are carried out with alternating dwell and advancing intervals with filling taking place at the filling station and elevating taking place at the elevating station during the dwell intervals while an empty lower dish member and a lid member spaced thereover are transported from the dish-drop station to the filling station, and a filled dish member with a lid member spaced thereover are advanced from the filling station to the elevating station during the advancing intervals.

7. In a method as recited in claim 6 and wherein the movable support is turned through an angle of 120° during each advancing interval.

8. In a method as recited in claim 1 and including the step of interrupting the movement of a filled lower dish member from the filling station to the elevating station at least once while providing a relatively abrupt stop in the movement of the filled lower dish member for distributing agar therein more uniformly.

9. In an apparatus for filling petri dishes, stationary support means situated at a dish-drop station for supporting at the latter station a stack of empty petri dishes each of which includes a lower dish member and an upper lid member normally covering and extending loosely downwardly around the lower dish member, with the lowermost petri dish of said stack situated on said stationary support means and the remainder of the stack of empty petri dishes resting on the lowermost petri dish, moving means situated in part over said stationary support means and engaging the lowermost petri dish of the stack of empty petri dishes for moving the lowermost petri dish along a predetermined path beyond said stationary support means, stationary holding means also situated over said stationary support means, with said moving means extending in part between said stationary support means and said stationary holding means, said stationary holding means engaging the next petri dish of the stack which is above the lowermost petri dish for preventing said next petri dish from moving with said lowermost petri dish beyond said stationary support means while freeing said next petri dish and the remainder of the petri dishes of the empty stack to drop onto said stationary support means after said moving means has moved the lowermost petri dish beyond said stationary support means, movable support means operatively connected with said moving means for movement therewith, said movable support means being situated in part beneath said stationary support means at a predetermined elevation beneath said moving means while moving with the latter along said predetermined path, said moving means while moving the lowermost petri dish beyond said stationary support means at the same time preventing said lid member of said lowermost petri dish from falling to an elevation below said moving means while freeing the lower dish member of the lowermost petri dish to fall from the lid member, thereof onto said movable support means to be carried thereby at a given space below the lid member which is retained by said moving means while the lid member and the dish member which has dropped therefrom are moved together, while being maintained in vertical alignment one above the other, along said predetermined path, the distance of said movable support means beneath said moving means being sufficient to provide a given space between the lid member moved by the moving means and the dropped dish member carried by the movable support means, said moving means moving the lid member carried thereby as well as said movable support means to a filling station, filling means situated at said filling station for filling a given quantity of agar into the dish member situated on and carried by said movable support means, said filling means including a discharge nozzle which extends into the space between the upper lid member and lower dish member of the petri dish situated at the filling station, said moving means then moving the lid member carried thereby and the movable support means with the filled dish member thereon to an elevating station situated beyond said filling station, said movable support means being formed with an opening which is situated beneath the filled dish member carried thereby, and elevating means situated at said elevating station and being movable in part upwardly through said opening of said movable support means for elevating the filled dish member at the elevating station upwardly beyond said movable support means and into the lid member carried by said moving means for closing the filled petri dish while continuing the elevation thereof upwardly beyond the movable support means, and stationary plate means situated over said moving means at said elevating station and formed with an opening through which said elevating means displaces the filled, closed petri dish upwardly beyond said stationary plate means, said elevating means after situating the closed, filled petri dish at a given elevation above said plate means then moving back down through said opening of said plate means and downwardly beyond said moving means through said opening of said movable support means to a rest position situated below said movable support means, said plate means carrying at said opening thereof a means for preventing the closed, filled petri dish which has been moved by said elevating means to said given elevation above said plate means back down beyond said plate means, so that the filled, closed petri dish remains resting on said stationary plate means over said opening thereof, said moving means sequentially moving each petri dish of the empty stack which drops onto said stationary support means beyond the latter to the filling station with the lower dish member of each petri dish moved beyond said stationary support means dropping onto said movable support means and being filled at the filling station while each filled lower dish member arriving at said elevating station is elevated by said elevating means, whereby a stack of empty petri dishes at the dish-drop station drop one by one onto said stationary support means with the stack of empty petri dishes becoming gradually shorter, while a stack of filled petri dishes is formed one by one on said plate means at the elevating station and becomes gradually taller.

10. The combination of claim 9 and wherein said plate means has a portion which forms said holding means, said portion of said plate means being situated over said stationary support means and being formed with an opening in which the next petri dish above the lowermost petri dish on said support means is situated so that said portion of said plate means prevents said next petri dish from being moved beyond said stationary support means by said moving means.

11. The combination of claim 10 and wherein a carousel means is situated over said plate means for holding on said plate means a circular row of initially empty stacks of petri dishes with the first stack of said circular row situated at said dish-drop station which the last stack of said circular row is situated beyond said elevating station, said elevating means forming a stack of filled petri dishes in said carousel means on said plate means from a stack of empty petri dishes at the dish-drop station, and turning means operatively connected to said carousel means for turning the latter about a central upright axis about which the circular row of petri dishes held by said carousel means is arranged, said turning means operating said carousel means to turn a second stack of empty petri dishes to said dish-drop station after a stack of empty petri dishes previously situated at the dish-drop station becomes exhausted, with said carousel means simultaneously turning a stack of filled petri dishes away from the elevating station so as to leave at the elevating station a free space to receive the next stack of filled petri dishes, said turning means being operatively connected with said carousel means for turning the latter at predetermined intervals through increments which will result in filling of all of the stacks of empty petri dishes.

12. The combination of claim 9 and wherein while said moving means moves a filled lower dish member of a petri dish with the lid thereover from said filling station to said elevating station, said moving means simultaneously displaces an empty petri dish from the dish-drop station beyond said support means to the filling station with the lower dish member of the petri dish moved to the filling station dropping from the lid member held by the moving means onto the movable support means to be transported to the filling station while carried by the movable support means.

13. The combination of claim 12 and wherein while said elevating means elevates a filled lower dish member into a lid member and then elevates the closed, filled petri dish to said given elevation above said plate means, said filling means is filling a lower dish member at said filling station.

14. The combination of claim 13 and wherein said moving means turns about a predetermined upright axis and includes an upper plate member having portions which are angularly spaced from each other about said upright axis and which successively move through a space between said stationary support means and said holding means, said portions of said upper plate member each being formed with an opening large enough to surround a lower dish member of a petri dish resting on said stationary support means with a given clearance while small enough to engage the lower edge of an upper lid member of a petri dish whose lower dish member rests on said stationary support means, said movable support means being in the form of a lower plate member operatively connected with said upper plate member for turning movement therewith and situated beneath the same by a distance sufficient to provide for dropping of a lower dish member displaced beyond said stationary support means onto said lower plate member while being maintained at a given elevation below a lower lid member carried by said upper plate member of said movable support means, whereby as each portion of said upper plate member displaces a lid of a lowermost petri dish of a stack of empty petri dishes on said stationary support means beyond the latter, the next portion of said upper plate means moves beneath the next petri dish held by said holding means.

15. The combination of claim 14 and wherein said upper plate member of said moving means includes three of said portions spaced equidistantly about said upright axis and said moving means having dwell intervals during which said three portions remain stationary for a given interval at said stations, respectively, with said moving means having between said dwell intervals advancing intervals during which said moving means turns about said upright axis through 120°.

16. The combination of claim 9 and wherein said stationary support means is in the form of a plate which is stationary and which has an edge beyond which the lowermost petri dish of a stack on said plate is moved by said moving means, said edge of said plate being formed with an arcuate portion conforming substantially to the curvature of the lower dish member of the lowermost petri dish on the plate and past which the lower dish member falls onto said movable support means so that the falling of the lower dish member takes place at the time earlier than would be the case if said edge of said plate were straight.

17. The combination of claim 9 and wherein detecting means is situated in the path of movement of one of said petri dish members from said dish-drop station to said filling station for detecting the presence of said one member and for terminating the operation of said moving means in the event that a member is not detected.

18. The combination of claim 9 and wherein said filling means includes a pump for pumping a given quantity of agar into a lower dish member at said filling station, and calibrating means operatively connected to said pump for calibrating the latter to determine the magnitude of the quantity of agar delivered to the lower dish member at the filling station.

19. The combination of claim 18 and wherein said calibrating means is an optical calibrating means including a rotary circular plate formed with notches in its periphery and an optical sensing means for sensing said notches.

20. The combination of claim 9 and wherein said means carried by said plate means for preventing a filled petri dish from moving downwardly beyond said plate means includes at least one member hinged to said plate means at said opening thereof and turnable upwardly with respect to said plate means but not downwardly beyond said plate means.

21. The combination of claim 9 and wherein said elevating means includes a lifting plunger movable up through said opening of said movable support means and up through said opening of said plate means, guide means operatively connected with said plunger for guiding the latter for vertical movement, lever means operatively connected with said plunger for moving the same vertically on said guide means, and drive means operatively connected to said lever means for turning the latter about a predetermined horizontal axis.

22. The combination of claim 11 and wherein said moving means together with said movable support means are turnable about an upright axis which is parallel to and spaced from the central axis of said carousel means.

23. The combination of claim 11 and wherein the stacks of petri dishes at said carousel means are spaced angularly about said central axis by equal angular distances and said elevating station being situated from said dish-drop station about said central axis by the same angular distance as the angular distance between successive stacks of petri dishes at said carousel means, so that stacking spaces of said carousel means for receiving stacks of petri dishes can all be filled except that one which becomes situated at the elevating station.

24. The combination of claim 11 and wherein said stationary support means and said elevating means are both situated at least in part beneath said carousel means while said filling station is situated outwardly beyond said carousel means with said moving means and said movable support means therewith moving each petri dish from said dish-drop station outwardly away from said carousel means to said filling station and then back toward said carousel means to said elevating station.

* * * * *